(12) United States Patent
Bowers et al.

(10) Patent No.: US 6,423,761 B1
(45) Date of Patent: *Jul. 23, 2002

(54) CONTACT LENS MATERIAL

(75) Inventors: Roderick William Jonathon Bowers; Peter William Stratford; Stephen Alister Jones, all of Uxbridge (GB)

(73) Assignee: Biocompatibles Limited, Uxbridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 08/469,861

(22) Filed: Jun. 6, 1995

Related U.S. Application Data

(62) Division of application No. 08/050,032, filed on Apr. 28, 1992, now Pat. No. 6,240,453.

(30) Foreign Application Priority Data

Oct. 29, 1990 (GB) ............................................. 9023498
Oct. 29, 1991 (WO) .............................. PCT/GB91/01887

(51) Int. Cl.$^7$ ........................... C08L 43/00; C08F 12/30
(52) U.S. Cl. ..................... 523/106; 524/547; 526/277; 526/287
(58) Field of Search ................................ 526/277, 287; 523/106; 524/547

(56) References Cited

U.S. PATENT DOCUMENTS

| | | | |
|---|---|---|---|
| 3,671,502 A | | 6/1972 | Samour et al. |
| 4,038,264 A | | 7/1977 | Rostokker et al. .......... 260/79.3 |
| 4,071,508 A | * | 1/1978 | Steckler ...................... 526/277 |
| 4,152,508 A | | 5/1979 | Ellis et al. ................... 526/279 |
| 4,205,152 A | * | 5/1980 | Mizuguchi et al. .......... 526/265 |
| 4,786,657 A | * | 11/1988 | Hammar et al. ............... 522/90 |
| 4,863,980 A | | 9/1989 | Cowan et al. |
| 5,270,415 A | | 12/1993 | Sulc et al. |
| 5,380,904 A | | 1/1995 | Chapman et al. |
| 5,391,669 A | | 2/1995 | Sulc et al. |
| 5,422,402 A | | 6/1995 | Bowers et al. |
| 5,453,467 A | | 9/1995 | Bamford et al. |

FOREIGN PATENT DOCUMENTS

| | | |
|---|---|---|
| CA | 1167838 | 5/1984 |
| EP | 0 032 443 | 1/1981 |
| EP | 0 350 030 | 1/1990 |
| EP | 0 370 827 | 1/1990 |
| EP | 0537972 | 4/1993 |
| JP | 5943342 | 1/1984 |
| JP | 60179408 | 1/1985 |
| JP | 60204711 | 1/1985 |
| JP | 6067489 | 4/1985 |
| JP | 6021599 | 5/1985 |
| JP | 339309 | 2/1991 |

OTHER PUBLICATIONS

Ishihara et al., "Improvement of Blood Compatibility on Cellulose Dialysis Membrane," *Biomaterials*, vol. 13, No. 3, pp. 145–149 (1992).

Kojima et al., "Interaction Between Phospholipids and Biocompatible Polymers Containing a Phosphorylcholine Moiety," *Biomaterials*, vol. 12, pp. 121–124 (Mar.).

Ishihara et al., "Preparation of Phospholipid Polymers and Their Properties as Polymer Hydrogel Membranes," *Polymer Journal*, vol. 22, No. 5, pp. 355–360 (1990).

Ishihara et al., "Protein Adsorption from Human Plasma is Reduced on Phospholipid Polymers," *The 17th Annual Meeting of the Society for Biomaterials*, May 1–5, 1991, pp. 297–298.

Wielema et al., "Zwitterionic Polymers—I. Synthesis of a Novel Series of Poly(Vinylsulphobetaines). Effect of Structure of Polymer on Solubility in Water," *Eur. Polym. J.*, vol. 23, No. 12, pp. 947–950 (1987).

*Kobunshi Ronbunshu*, vol. 40, No. 12, pp. 785–793 (Dec. 1983) with English Abstract.

*Kobunshi Ronbunshu*, vol. 35, No. 7, pp. 423–427 (Jul. 1978) with English Abstract.

Ishihara et al., "Reduced Thrombogenicity of Polymers Having Phospholipid Polar Groups," *Journal of Biomedical Materials Research*, vol. 24, pp. 1069–1077 (1990).

Nakabayashi et al., "Mechanism of Nonthrombogenicity on 2–Methacryloyloxyethyl Phosphorylcholine Copolymers," *The 17th Annual Meeting of the Society for Biomaterials*, May 1–5, 1991, p. 296.

\* cited by examiner

*Primary Examiner*—Peter D. Mulcahy
(74) *Attorney, Agent, or Firm*—Sughrue Mion, PLLC

(57) ABSTRACT

Cross-linked copolymers which are obtainable by polymerising a neutral diluent monomer or monomers, a monomer or monomers bearing a center of permanent positive charge, and a bifunctional and/or trifunctional cross-linking agent, are suitable for use in contact lenses. Process for producing them by copolymerization, contact lens material comprising them, contact lenses made of them and processes for producing contact lenses from them.

77 Claims, No Drawings

CONTACT LENS MATERIAL

This is a divisional of application Ser. No. 08/050,032 filed Apr. 28, 1992 now U.S. Pat. No. 6,420453.

The present invention relates to copolymers, in particular suitable for use in contact lenses.

The use of synthetic hydrogels for contact lenses was first demonstrated by Wichtecte and Lim in the 1960's. Early hydrogels employed 2-hydroxyethyl methacrylate (HEMA) as principal monomer, together with some of the homologous esters of the glycol monomethacrylate series such as diethylene glycol monomethacrylate and tetraethylene glycol monomethacrylate. It was later found that slightly crosslinked copolymers of the higher glycol monomethyacrylates and 2-hydroxyethyl methacrylate yielded transparent hydrogels that swelled in water to a higher hydration than the hydrogels of 2-hydroxyethyl methacrylate.

The water content of hydroxyalkyl methacrylate based gels can be further increased by the addition of vinyl lactams, methacrylic acids, acrylic acids, acrylamides and methacrylamides. Although the required degree of gel hydration can be achieved by the addition of anionic monomers, it is well known that these gels display high levels of protein deposition on and occasionally within the gel matrix.

It has now surprisingly been found that effective contact lens materials which have both good transparency and a high degree of water swellability are provided by copolymers which have a permanent positive charge built into them. Such polymers are formed by polymerising and crosslinking a neutral diluent monomer, for example HEMA, with a co-monomer bearing a centre of permanent positive charge. These formulations have been found to have a high level of protein resistance to tear component deposition and a reduction in lens water loss.

Accordingly, the present invention provides a crosslinked copolymer which is obtainable by polymerising a neutral diluent monomer or monomers, a monomer or monomers bearing a centre of permanent positive charge, and a bifunctional or trifunctional crosslinking agent.

The crosslinked copolymers of the present invention therefore comprise residues of a diluent monomer or monomers, a monomer or monomers bearing a centre of permanent positive charge, and a bifunctional or trifunctional crosslinking agent.

The copolymers of the invention may be xerogels which do not contain any water. Alternatively, they may be in the form of hydrogels which do contain water.

The invention also provides a process for producing such a crosslinked copolymer, a contact lens material comprising such a copolymer, a contact lens made from such a copolymer, and use of such a copolymer or contact lens material in the production of a contact lens.

Diluent Comonomer

The diluent monomer can act as a solvent for the comonomers during copolymerisation to produce the copolymer if no additional solvent is present. Where the diluent monomer and monomer bearing the centre of permanent positive charges are immiscible a solvent can be used to aid mixing.

Particular examples of diluent comonomers include alkyl (alk)acrylate preferably containing 1 to 12, more preferably 1 to 4, carbon atoms in the alkyl group of the ester moiety, such as a methyl (alk)acrylate and butyl (alk)acrylate; a dialkylamino alkyl (alk)acrylate, preferably containing 1 to 4 carbon atoms in each alkyl moiety of the amine and 1 to 4 carbon atoms in the alkylene chain, e.g. 2(dimethylamino) ethyl (alk)acrylate; an alkyl (alk)acrylamide preferably containing 1 to 4 carbon atoms in the alkyl group of the amide moiety; a hydroxyalkyl (alk)acrylate preferably containing from 1 to 4 carbon atoms in the hydroxy moiety, e.g. a 2-hydroxyethyl (alk)acrylate; or a vinyl monomer such as an N-vinyl lactam, preferably containing from 5 to 7 atoms in the lactam ring for instance vinyl pyrrolidone; styrene or a styrene derivative which for example is substituted on the phenyl ring by one or more alkyl groups containing from 1 to 4 carbon atoms, and/or by one or more halogen, such as fluorine atoms.

It is to be understood that throughout the specification (alk)acrylate, (alk)acrylic and (alk)acrylamide mean acrylate or alkacrylate, acrylic or alkacrylic and acrylamide or alkacrylamide respectively. Preferably alkacrylate, alkacrylic and alkacrylamide groups contain from 1 to 4 carbon atoms in the alkyl group thereof and are most preferably methacrylate, methacrylic or methacrylamide groups. Similarly (meth)acrylate, (meth)acrylic and (meth)acrylamide shall be understood to mean acrylate or methacrylate, acrylic or methacrylic and acrylamide or methacrylamide respectively.

Preferably the diluent monomer is selected from vinylpyrrolidone, 2-hydroxyethyl methacrylate, methyl methacrylate and mixtures thereof, most preferably 2-hydroxyethyl methacrylate, methyl methacrylate and mixtures thereof. In one embodiment diluent monomers are vinylpyrrolidone, 2-hydroxyethyl methacrylate and mixtures thereof.

Comonomers Bearing A Centre of Permanent Positive Charge

The comonomer bearing the centre of permanent positive charge can either be cationic or zwitterionic. In the latter case the monomer includes within its structure not only a centre of permanent positive charge but also a centre of negative charge. Typically the centre of permanent positive charge in both cationic and zwitterionic comonomers is provided by a quaternary nitrogen atom.

Preferred comonomers which bear a centre of positive charge are of general formula (I)

$$Y-B-X \qquad (I)$$

wherein

B is a straight or branched alkylene, oxaalkylene or oligo-oxaalkylene chain or if X contains a carbon-carbon chain between B and the centre of permanent positive charge or if Y contains a terminal carbon atom, a valence bond, X is a group bearing a centre of permanent positive charge and Y is an ethylenically unsaturated polymerisable group selected from

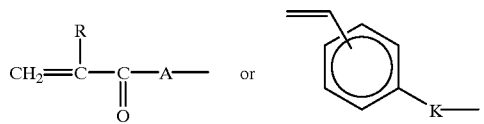

wherein:

R is hydrogen or a $C_1$–$C_4$ alkyl group;

A is —O— or —$NR^1$— where $R^1$ is hydrogen or a $C_1$–$C_4$ alkyl group or $R^1$ is —B—X where B and X are as defined above.

K is a group —$(CH_2)_pCO(O)$—, —$(CH_2)_pC(O)O$—, —$(CH_2)_pOC(O)O$—, —$(CH_2)_pNR^2$—, —(CH$_2$)$_p$NR$^2$C(O)—, —(CH$_2$)$_p$C(O)NR$^2$—, (CH$_2$)$_p$NR$^2$C(O)O—, —(CH$_2$)$_p$OC(O)NR$^2$—, —(CH$_2$)$_p$NR$^2$C(O)NR$^2$— (in which the groups R$^2$ are the same or different), —(CH$_2$)$_p$O—, —(CH$_2$)$_p$SO$_3$—, or, optionally in a combination with B, a valence bond, and p is from 1 to 12 and R$^2$ is hydrogen or a C$_1$–C$_4$ alkyl groups The proviso on whether B may be a valence bond ensures that the centre of permanent positive charge in X is not directly bonded to a heteroatom, such as an oxygen or nitrogen atom in Y.

Preferred monomers which bear a centre of positive charge are those of general formula (II) or (III).

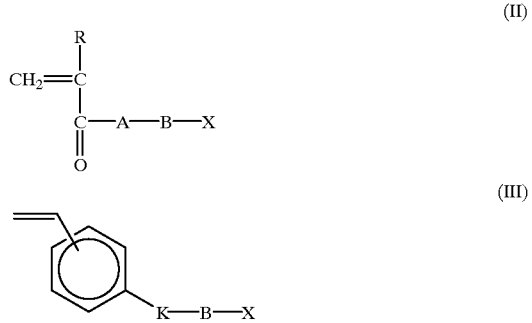

where R, A, B and X are as defined with reference to formula (I).

Preferably R is hydrogen, methyl, or ethyl, more preferably methyl, so that the monomer of formula (II) is an acrylic acid, methacrylic acid or ethacrylic acid derivative.

In the compounds of formula (III) K may be a valence bond and B a group, K may be a group and B a valence bond, both K and B may be groups or K and B may together be a valence bond. Preferably B is a group where K is a valence bond. Where K is a group then preferably p is from 1 to 6, more preferably 1, 2 or 3 and most preferably p is 1. When K is a group —(CH$_2$)$_p$NR$^2$—, —(CH$_2$)$_p$NR$^2$C(O)—, —(CH$_2$)$_p$C(O)NR$^2$—, —(CH$_2$)$_p$NR$^2$C(O)O—, —(CH$_2$)$_p$OCNR$^2$— or —(CH$_2$)$_p$NR$^2$C(O)NR$^2$— then R$^2$ is preferably hydrogen, methyl or ethyl, more preferably hydrogen.

Preferably B is:

an alkylene group of formula —(CR$^3_2$)$_a$—, wherein the groups —(CR$^3_2$)— are the same or different, and in each group —(CR$^3_2$)— the groups R$^3$ are the same or different and each group R$^3$ is hydrogen or C$_{1-4}$ alkyl, preferably hydrogen, and a is from 1 to 12, preferably 1 to 6;

an oxaalkylene group such as alkoxyalkyl having 1 to 6 carbon atoms in each alkyl moiety, more preferably —CH$_2$O(CH$_2$)$_4$—;

an oligo-oxaalkylene group of formula —[(CR$^4_2$)$_b$O]$_c$(CR$^4_2$)$_b$— where the groups —(CR$^4_2$)— are the same or different and in each group —(CR$^4_2$)— the groups R$^4$ are the same or different and each group R$^4$ is hydrogen or C$_{1-4}$ alkyl, preferably hydrogen, and b is 2 or 3 and c is from 2 to 11, preferably 2 to 5;

or a valence bond but only if X contains a carbon-carbon chain between B and the centre of positive charge, or if Y contains a terminal carbon atom.

Preferred groups B include a valence bond and alkylene, oxaalkylene and oligo-oxaalkylene groups of up to 12 carbon atoms.

Preferred groups X are the groups of formula (IVA), (IVB), (IVC), (IVD), (IVE) and (IVF) as defined below, of which the groups of formula (IVC) are particularly preferred.

The groups of formula (IVA) are:

where the groups R$^5$ are the same or different and each is hydrogen or C$_{1-4}$ alkyl and Z$^\ominus$ is a counterion.

Preferably the groups R$^5$ are all the same. It is also preferable that at least one of the groups R$^5$ is methyl, and more preferable that all the groups R$^5$ are methyl.

The counterion Z$^\ominus$ present in the compounds of formula (II) or (III) containing a group of formula (IVA) is such that the compounds are neutral salts. The counterion may be exchanged with ions in physiological fluids and thus the specific nature of the counterion is not critical in the present invention. However, physiologically acceptable counterions are preferred. Suitable physiologically acceptable counterions include halide anions, such as chloride, bromide or fluoride ions, other inorganic anions such as sulphate, phosphate and phosphite and organic anions such as aliphatic mono-, di- or tri-carboxylate anions containing from 2 to 25 carbon atoms and optionally bearing one or more hydroxyl groups e.g. acetate, citrate and lactate.

When X is a group of formula (IVA), preferably B is a group of formula —(CR$^3_2$)— or —(CR$^3_2$)$_2$—, eg. —(CH$_2$)— or —(CH$_2$CH$_2$)—.

The groups of formula (IVB) are:

where the groups R$^6$ are the same or different and each is hydrogen or C$_{1-4}$ alkyl and d is from 2 to 4.

Preferably the groups R$^6$ are the same. It is also preferable that at least one of the groups R$^6$ is methyl, and more preferable that the groups R$^6$ are both methyl.

Preferably d is 2 or 3, more preferably 3.

When X is a group of formula (IVB) preferably B is a group of formula —(CR$^3_2$)— or —(CR$^3_2$)$_2$—, eg. —(CH$_2$)— or —(CH$_2$CH$_2$)—.

The groups of (OVA) are:

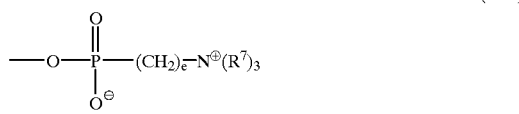

where the groups R$^7$ are the same or different and each is hydrogen or C$_{1-4}$ alkyl, and e is from 1 to 4.

Preferably the groups R$^7$ are the same. It is also preferable that at least one of the groups R$^7$ is methyl, and more preferable that the groups R$^7$ are all methyl.

Preferably e is 2 or 3, more preferably 2.

When X is a group of formula (IVC) preferably B is a group of formula —(CR$^3_2$)— or —(CR$^3_2$)$_2$—, eg. —(CH$_2$)— or —(CH$_2$CH$_2$)—.

The groups of formula (IVD) are:

$$-[O]_z-CH \begin{matrix} CH_2-O-\overset{O}{\underset{O^\ominus}{P}}-O-(CH_2)_f-{}^\oplus N(R^8{}_3) \\ \\ CH_2-O-\underset{O}{\overset{\|}{C}}-B^1-CH_3 \end{matrix} \quad (IVD)$$

wherein the groups $R^8$ are the same or different and each is hydrogen or $C_{1-4}$ alkyl, $B^1$ is a valence bond or straight or branched alkylene, oxaalkylene or oligo-oxaalkalkylene group, f is from 1 to 4 and if B is other than a valence bond, Z is 1 and if B is a valence bond Z is 0 if X is directly bonded to an oxygen or nitrogen atom, and otherwise Z is 1.

Preferably the groups $R^8$ are the same. It is also preferable that at least one of the groups $R^8$ is methyl, and more preferable that the groups $R^8$ are all methyl.

Preferably f is 1 or 2, more preferably 2.

Preferably $B^1$ is:

a valence bond;

an alkylene group of formula $-(CR^{3a}{}_2)_{aa}-$, wherein the groups $-(CR^{3a}{}_2)-$ are the same or different, and in each group $-(CR^{3a}{}_2)-$ the groups $R^{3a}$ are the same or different and each group $R^{3a}$ is hydrogen or $C_{1-4}$ alkyl, preferably hydrogen, and aa is from 1 to 24, preferably 6 to 18;

an oxaalkylene group such as alkoxyalkyl having 1 to 6 carbon atoms in each alkyl moiety, more preferably $-CH_2O(CH_2)_4-$; or an oligo-oxaalkylene group of formula $-[(CR^{4a}{}_2)_{ba}O]_{ca}-$ where the groups $-(CR^{4a}{}_2)-$ are the same or different and in each group $-(CR^{4a}{}_2)-$ the groups $R^{4a}$ are the same or different and each group $R^{4a}$ is hydrogen or $C_{1-4}$ alkyl, preferably hydrogen, and ba is 2 or 3 and ca is from 1 to 12, preferably 1 to 6.

Preferred groups $B^1$ include a valence bond and alkylene, oxaalkylene and oligo-oxaalkylene groups of up to 24 carbon atoms.

In one embodiment B and $B^1$ are the same.

The groups of formula (IVE) are:

$$-[O]_z-CH_2-CH-CH_2-O-\overset{O}{\underset{O^\ominus}{\overset{\|}{P}}}-O-(CH_2)_g-{}^\oplus N(R^9)_3 \atop \underset{O}{\overset{|}{O}}-\underset{O}{\overset{\|}{C}}-B^2-CH_3 \quad (IVE)$$

wherein the groups $R^9$ are the same or different and each is hydrogen or $C_1$–$C_4$ alkyl, $B^2$ is a valence bond or a straight or branched alkylene, oxaalkylene or oligo-oxaalkylene group, g is from 1 to 4 and if B is other than a valence bond, Z is 1 and if B is a valence bond Z is 0 if X is directly bonded to an oxygen or nitrogen atom and otherwise Z is 1.

Preferably the groups $R^9$ are the same. It is also preferable that at least one of the groups $R^8$ is methyl, and more preferable that the groups $R^8$ are all methyl.

Preferably g is 1 or 2, more preferably 2.

Preferably $B^2$ is:

a valence bond;

an alkylene group of formula $-(CR^{3b}{}_2)_{ab}-$, wherein the groups $-(CR^{3b}{}_2)-$ are the same or different, and in each group $-(CR^{3b}{}_2)-$ the groups $R^{3b}$ are the same of different and each group $R^{3b}$ is hydrogen or $C_{1-4}$ alkyl, preferably hydrogen, and ab is from 1 to 24, preferably 6 to 18, an oxaalkylene group such as alkoxyalkyl having 1 to 6, carbon atoms in each alkyl moiety, more preferably $-CH_2O(CH_2)_4-$; or an oligo-oxaalkylene group of formula $-[(CR^{4b}{}_2)_{bb}O]_{cb}-$ where the groups $-(CR^{4b}{}_2)-$ are the same or different and in each group $-(CR^{4b}{}_2)-$ the groups $R^{4b}$ are the same or different and each group $R^{4b}$ is hydrogen or $C_{1-4}$ alkyl, preferably hydrogen, and bb is 2 to 6 and cb is from 1 to 12, preferably 1 to 6.

Preferred groups $B^2$ include a valence bond and alkylene, oxaalkylene and oligo-oxaalkylene groups of up to 24 carbon atoms.

In one embodiment B and $B^2$ are the same.

The groups of formula (IVF) are:

$$CH_3-B^3-\overset{O}{\overset{\|}{C}}-O-CH_2 \atop \underset{-[O]_z-CH_2}{\overset{|}{CH}-O-\overset{O}{\underset{O^\ominus}{\overset{\|}{P}}}-O-(CH_2)_h N^\oplus(R^{10})_3} \quad (IVF)$$

wherein the groups $R^{10}$ are the same or different and each is hydrogen or $C_{1-4}$ alkyl, $B^3$ is a valence bond or a straight or branched alkylene, oxaalkylene or oligo-oxaalkylene group, h is from 1 to 4 if B is other than a valence bond, Z is 1 and if B is a valence bond Z is 0 if X is directly bonded to an oxygen or nitrogen atom and otherwise Z is 1.

Preferably the groups $R^{10}$ are the same. It is also preferable that at least one of the groups $R^{10}$ is methyl, and more preferable that the groups $R^{10}$ are all methyl.

Preferably h is 1 or 2, more preferably 2.

Preferably $B^3$ is:

a valence bond;

an alkylene group of formula $-(CR^{3c}{}_2)_{ac}-$, wherein the groups $-(CR^{3c}{}_2)-$ are the same or different, and in each group $-(CR^{3c}{}_2)-$ the groups $R^{3c}$ are the same or different and each group $R^{3c}$ is hydrogen or $C_{1-4}$ alkyl, preferably hydrogen, and ac is from 1 to 24, preferably 6 to 18;

an oxaalkylene group such as alkoxyalkyl having 1 to 6 carbon atoms in each alkyl moiety, more preferably $-CH_2O(CH_2)_4-$; or an oligo-oxaalkylene group of formula $-[(CR^{4c}{}_2)_{bc}O]_{cc}-$ where the groups $-(CR^{4c}{}_2)-$ are the same or different and in each group $-(CR^{4c}{}_2)-$ the groups $R^{4c}$ are the same or different and each group $R^{4c}$ is hydrogen or $C_{1-4}$ alkyl, preferably hydrogen, and be in 2 to 6 and cc is from 1 to 12, preferably 1 to 6.

Preferred groups $B^3$ include a valence bond and alkylene, oxaalkylene and oligo-oxaalkylene groups of up to 24 carbon atoms.

In one embodiment B and $B^3$ are the same.

According to one particular embodiment, the monomer bearing a centre of permanent positive charge is a monomer of formula (V)

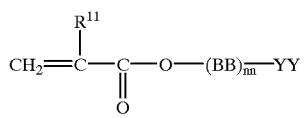
(V)

wherein BB is a straight or branched $C_1$–$C_6$ alkylene chain optionally interrupted by one or more oxygen atoms;

nn is from 1 to 12

$R^{11}$ is H or a $C_1$–$C_4$ alkyl group; and

YY is a group which includes a centre of positive charge. More preferably,

YY is a group selected from:

—$^{\oplus}$N(CH$_3$)$_3$; (VIA)

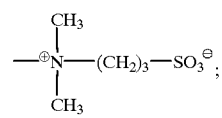
(VIB)

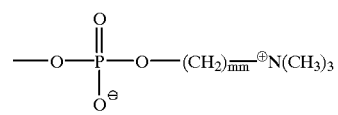
(VIC)

in which mm is from 1 to 4;

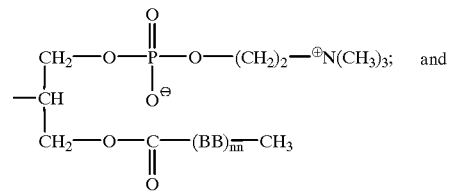
(VID) and

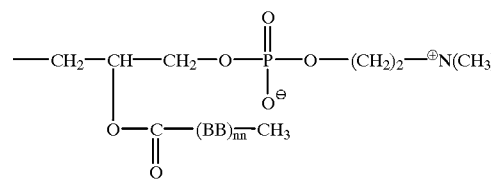
(VIE)

the group BB in (VID) and (VIE) being a linear or branched alkylene chain as defined above and nn being as defined above.

Preferably BB is a group selected from —CH$_2$—, —C(R$^{12}$)$_2$—, in which R$^{12}$ is C$_{1-4}$ alkyl, and —CH$_2$—CH$_2$—O—.

Preferably in compounds of formula (V), R$^{11}$ is hydrogen or methyl.

When X is a group as defined under (VID) or (VIE), the group (BB)$_{nn}$ is preferably chosen to avoid steric hindrance in the vicinity of the adjacent —OC(O)— group, the reactivity of which could be adversely affected by such steric hindrance.

Preferred examples of co-monomers of formula (I) are:

Compound A

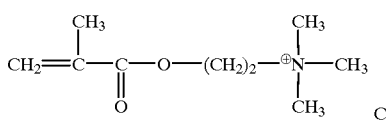

Compound B

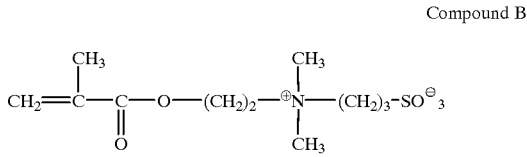

Compound C

Compounds D

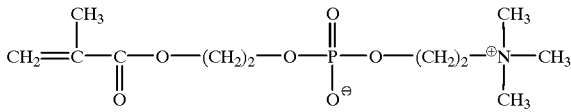

Compounds E

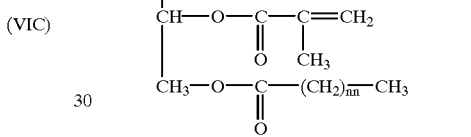

Compounds F

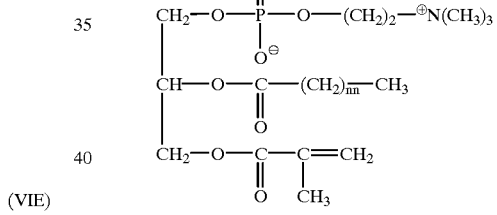

Compounds G

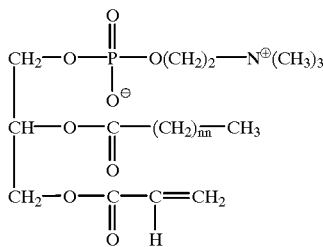

Particular examples of preferred comonomers bearing a centre of permanent positive charge are 2 (methacryloyloxy) ethyl-2'(trimethylammonium)ethyl phosphate inner salt

[Compound C above] and 1[4(4'-vinylbenzyloxy)butane]-2"(trimethylammonium)ethyl phosphate inner salt [a compound of formula (III)].

Comonomers bearing a centre of permanent positive charge, such as those of formulae (II) and (III), and comonomers of formula (V) may be prepared by conventional techniques using known reactions, for example using a suitable substituted alkyl (alk)acrylate, glycerophosphoryl choline or suitable substituted styrene as starting material.

Examples of suitable substituted alkyl (alk)acrylates include dimethylaminoethyl(meth)acrylate and 2-hydroxyethyl(meth)acrylate.

Comonomers of formula (II) or (III) containing a group of formula (IVA), (IVB) or (IVC) and comonomers of formula (V) including a group of formula (VIA), (VIB), and (VIC) may be prepared as described in Reference Examples 1 to 4 or by analogous known methods.

Comonomers of formula (II) or (III) containing a group of formula (IVD) and comonomer of formula (V) including a group of formula (VID) may be prepared by selective acylation of glycerophosphorylcholine or analogues thereof at the primary hydroxyl group with an activated acid derivative such as an acid anhydride $O[C(O)B^1CH_3]_2$ or an acid halide $CH_3B^1COHal$ where $B^1$ is as defined above and Hal is halogen, followed by acylation of the secondary hydroxyl group with an appropriate acylating agent, for example methacryloyl chloride. Purification, for example by column chromatography on a suitable support, may be performed after each acylation or after the second acylation only. Suitable activated acid derivatives include acid anhydrides, acid halides, reactive esters and imidazolides. The acylations may be performed in a suitable anhydrous, aprotic solvent, for example N,N-dimethylformamide, optionally in the presence of a suitable non-nucleophilic base, for example triethylamine.

Alternatively, the primary alcohol group in glycerophosphoryl choline or an analogue thereof may be blocked by reaction with a suitable protecting group reagent, for example t-butyldimethylsilyl chloride, under standard conditions and the secondary hydroxy group then treated with at acylating agent such as methacryloyl chloride. The t-butyldimethylsilyl protecting group may be removed by treatment with a dilute organic or mineral acid, for example p-toluene sulphonic acid, hydrochloric acid or with tetrabutylammonium fluoride. The deblocked primary hydroxyl group may then be treated with an activated acid derivative such as an acid anhydride $O[C(O)B^1CH_3]_2$ or acid halide $CH_3B^1COHal$ where $B^1$ is as defined above, and Hal is halogen.

Analogues of glycerophosphorylcholine may be prepared by reaction of phosphorus oxychloride with a bromoalcohol in an inert aprotic solvent, such as dichloromethane, to give a bromoalkylphosphorodichloridate. The dichloro derivative thus produced may then be treated with 2,2-dimethyl 1,3-dioxolane-4-methanol in the presence of a base, for example triethylamine, followed by acid hydrolysis to give a bromoalkylphosphorogylcerol derivative. This may then be treated with an amine $NR^8_3$, where $R^8$ is as defined above, for example trimethylamine, to generate the glycerophosphorylcholine analogue. This preparation is depicted in the following scheme.

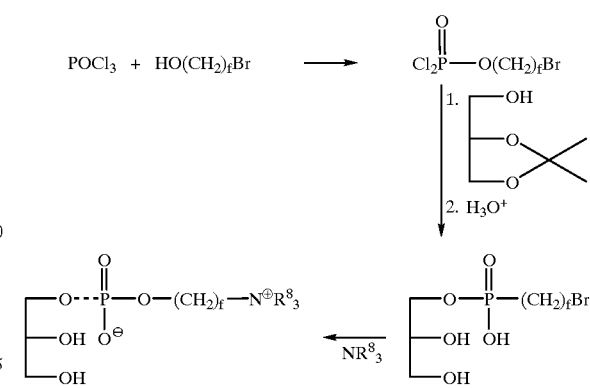

where $R^8$ and f are as defined in relation to groups of formula (IVD)

Comonomers of formula (II) or (III) containing a group of formula (IVE) and comomers of formula (V) containing a group of formula (VIE) may be prepared by the selective acylation of glycerophosphorylcholine or an analogue thereof at the primary hydroxyl group with for example, methacryloyl chloride followed by reaction at the secondary hydroxyl group using an activated acid derivative, such as an acid halide $O[C(O)B^2CH_3]_2$ or an acid halide $CH_3B^2COHal$, where $B^2$ is as defined above and Hal is halogen. The intermediates and final products may be purified, as necessary using column chromatography. Optionally, protecting group strategy, similar to that outlined above in relation to production of comonomers containing a group of formula (IVD), may be employed.

Comonomers of formula (II) or (III) containing a group of formula (IVF) may be prepared in an analogous manner to comonomers containing groups of formula (IVD) or (IVE).

Crosslinking Comonomers

The copolymers of the invention also comprise residues of difunctional and/or trifunctional comonomers. Such comonomers are capable of crosslinking the polymer during polymerisation. Conventional crosslinking agents may be used.

Examples of suitable crosslinking comonomers include alkane diol or triol di- or tri(alk)acrylates, eg (meth)acrylates, preferably containing 1 to 8 carbon atoms in the diol or triol residue; alkylene di- or tri(alk)acrylamides, e.g. (meth)acrylamides, preferably containing 1 to 6 carbon atoms in the alkylene group and and di- or tri-vinyl compounds such as di- or tri-vinyl benzene compounds. Particular examples of crosslinking agents include ethyleneglycoldimethacrylate, tetraethyleneglycol dimethacrylate, trimethylolpropanetrimethacrylate and N,N-methylenebisacrylamide.

Optionally the comonomer mixture used for polymerising the copolymer further comprises a gel swelling monomer such as an N-vinyl lactam, methacrylic acid or acrylic acid and where appropriate a bulking or solvating agent such as a solvent, for example, an alcohol or water.

Polymers of the invention may be prepared by copolymerising monomers bearing a centre of permanent positive change, diluent monomers and crosslinking monomers usually by bulk polymerisation in an appropriate mould. Additionally a solvent or solvent mixture may be included to provide a suitable reaction medium for immiscible comonomers. Suitable solvents include water, halogenated organic solvents and non-halogenated organic solvents. Initiators and/or reagents to modify the bulk morphology of the final polymer may also be included. Any conventional technique may be used for the polymerisation, typically thermal polymerisation or ultraviolet polymerisation.

The invention therefore further provides a method of preparing a crosslinked polymer which comprises copolymerising a monomer composition, such as a monomer solution, comprising a diluent monomer or monomers, a comonomer or comonomers including within its structure a centre of permanent positive charge, and a monomoner or monomers which will crosslink the resultant polymer. Optionally, the monomer composition further comprises a solvent or solvent mixture and a polymerisation initiator or initiators.

The monomer composition which is subjected to polymerisation typically comprises at least 30%, preferably at least 60%, and up to 99.79% by weight of diluent monomer. It typically comprises at least 0.2% and up to 50% monomer or monomers which contain a centre of permanent positive charge and from 0.01% to 20% by weight of crosslinking monomer. Optionally up to 10% by weight of gel swelling monomer is included.

In one embodiment the monomer composition which is subjected to polymerisation typically comprises at least 70%, preferably at least 80% by weight of the diluent monomer. It further comprises at least 0.2% and up to 20% of monomer or monomers which bear a centre of permanent positive charge and, optionally, up to 10% by weight of gel-swelling monomer or monomers.

The monomer composition may comprise conventional further polymer ingredients such as cross-linking agents and polymerisation initiators. These further ingredients are in one embodiment used in a total amount from 0.1 to 5%, typically from 0.2 to 3% and preferably about 0.5% by weight relative to the weight of the monomer composition prior to polymerisation.

Preferably the monomer composition comprises at least 0.01% and up to 10% of crosslinking monomer or monomers.

Examples of suitable initiators include bis(4-tertiarybutylcyclohexyl)-peroxydicarbonate, benzoylperoxide, 2,2'-azo-bis(2-methylpropionitrile) [i.e. azo-bis-isobutyro nitrile], 1-benzyl-2-hydroxy-2-dimethylethane-1-one and benzoin methylether. An initiator is generally used in a total amount from 0.1% to 5, typically from 0.2% to 3% and preferably about 0.5% by weight relative to the weight of the total monomer composition prior to polymerisation.

Additionally the monomer composition may have added to it a solvent or solvent mixture. Example's of suitable solvents are ethanol, methanol and water. When present, solvent suitably comprises from 0.1 to 50 weight % of the total reaction mixture, preferably from 5 to 40 weight %.

The polymer is prepared by dissolving the monomer or monomers bearing the centre of positive charge in the diluent monomer or monomers or diluent monomer/solvent mixture together with the crosslinking monomer or monomers and if present the polymerisation initiator or initiators. The solution thus formed is then purged with nitrogen, to remove any oxygen which may be present before the polymerisation process is begun. Polymerisation is carried out in a sheet-forming mould, a contact lens precursor button (thick round disc) mould, a contact lens mould or to provide a cylindrical polymer rod. For example, when carried out in a sheet-forming mould the monomer solution may be injected between two spaced plates and then polymerised in situ to generate a polymer sheet.

Generally the copolymers of the invention will be produced by copolymerisation in the absence water. This produces a xerogel material which can be moulded into contact lenses directly or moulded to give contact lens buttons which can be lathe cut using methods known in the art to produce contact lenses. The xerogel material may be washed in water or in aqueous buffer to remove any excess monomer and initiator. The xerogel material can be subsequently hydrated to produce hydrogel with an equilibrium water content of up to 90%, and preferably from 30 to 80%.

The polymers of the invention are both transparent and water swellable and therefore suitable for use as contact lens materials. In particular, the polymer may be suitable for use in contact lenses which are for example soft or gas permeable contact lenses.

The invention further provides contact lenses made from polymers of the invention as hereinbefore defined.

The invention may be further illustrated by the following examples.

EXAMPLE 1

Formation of 2(methacryloyloxyethyl)-2'(trimethylammonium)ethyl phosphate Inner Salt-co-2-hydroxyethylmethacrylate-co-ethylenegdycoldimethacrylate Buttons 2(methacryloyloxyethyl)-2'(trimethylammonium)ethyl phosphate inner salt (compound C) (4.86 g) was dissolved in 2-hydroxyethylmethacrylate (14.8 g), together with ethyleneglycodimethacrylate (0.25 g) and bis(4-tertiarybutylcyclohexyl)-peroxydicarbonate (0.048 g). This solution was de-gassed with nitrogen gas and then pipetted into an open stainless steel contact lens button mould. The mould was placed in an oven in a nitrogen atmosphere at 50° C. for 1¼ hours. After this time the mould was removed. The buttons were pushed out of the mould and the reaction completed by heating at 70° C. in a vacuum oven for 24 hours. The buttons were optically clear and could be machined to make contact lenses.

EXAMPLE 2

Formation of 2(methacroyloxyethyl)-2'(trimethylammonium)ethyl phosphate Inner Salt-co-2-hydroxyethylmethacrylate-co-ethyleneglycoldimethacrylate Buttons by photopolymerisation 2(methacryloyloxyethyl)-2'(trimethylammonium)ethyl phosphate inner salt (compound C) 5.00 g was dissolved in 2-hydroxyethylmethacrylate (14.2 g) together with ethyleneglycoldimethacrylate (0.2 g), 1-benzyl-2-hydroxy-2-dimethylethane-1-one (0.2 g) and bis(4-tertiarybutylcyclohexyl)-peroxydicarbonate (0.02 g). The solution was de-gassed with $N_2$ and then pipetted into an open stainless steel contact lens button mould. The monomer solutions were irradiated with a 100 w/inch medium pressure, mercury vapour lamp for 2 minutes. The reaction was completed thermally at 70° C. in a vacuum oven for 24 hours. The resulting buttons were machined to make contact lenses.

EXAMPLE 3

Formation of 2(methacryloyloxyethyl)-2'(trimethylammonium)ethyl phosphate Inner Salt-co-methylmethacrylate-co-ethyleneglycoldimethacrylate Buttons 2(methacryloyloxyethyl)-2'(trimethylammonium)ethyl phosphate inner salt (5.76 g) was dissolved in ethanol (6.5 ml) and methylmethacrylate (7.5 g). Ethyleneglycoldimethyacrylate (0.21 g), 1-benzyl-2-hydroxy-2-dimethylethane-1-one (0.2 g) and bis(4-tertiarybutylcyclohexyl)-peroxydicarbonate (0.01 g) were added to the solution and dissolved. The resulting solution was degassed with the gas and poured into an open stainless steel contact lens button mould. The solutions were then irradiated by a 100 W/inch medium pressure mercury vapour lamp for 2 minutes. The reaction was completed thermally at 70° C. in a vacuum oven for 24 hours. The ethanol was removed from these buttons by heating at 80° C. for 48 hours in a vacuum oven. The resulting buttons were machined to make contact lenses.

EXAMPLE 4

Formation of 2(methacryloyloxyethyl)-2'(trimethylammonium)ethyl phosphate Inner Salt-co-methylmethacrylate-co-ethyleneglycodimethylacrylate Rod A xerogel rod (1 cm diameter×10 cm) was produced as follows:

2(methacryloyloxyethyl)-2'(trimethylammonium)ethyl phosphate inner salt (compound C) (5.77 g) was mixed with ethanol (6.5 g), methylmethacrylate (7.4 g), ethyleneglycoldimethacrylate (0.2 g) and bis(4-tertiarybutylcyclohexyl)-peroxydicarbonate (0.03 g). The mixture was added to a polypropylene tube (1 cm diameter×10 cm) which was sealed at one end. $N_2$ gas was bubbled through the solution and then a cap placed over the end of the tube. The tube was then placed in an oven at 50° C. for 1.5 hours. After this time the gelled rod of polymer was removed from the tube.

The reaction was completed at 70° C. for 24 hours. After this time the rod was cut into 1 cm cylinders. These cylinders were heated in a vacuum oven at 80° C. for 48 hours in order to removed the ethanol. The resulting buttons were machined into lenses.

EXAMPLE 5

Formation of 2(methacryloyloxyethyl)-2'(trimethylammonium)ethyl phosphate Inner Salt-co-2-hydroxyethylmethacrylate-co-ethyleneglycoldimethylacrylate Membrane 2(methacryloxyethyl)-2(trimethylammonium)ethyl phosphate inner salt (compound C) (3.60 g) was dissolved in 2-hydroxyethylmethacrylate (6.27 g) together with ethyleneglycoldimethacrylate (0.12 g) as a crosslinking agent and azobisisobutyronitrile (0.2 g) as a polymerisation initiator. The resultant monomer solution was then deoxygenated by bubbling nitrogen through for 5 minutes.

The monomer solution thus prepared was injected into a mould formed by two glass sheets covered by spray mounted polyethyleneterephthalate sheet and separated using a polytetrafluoroethylene spacer. Polymerisation was carried out in situ by heating the mould to 80° C. for 2 hours.

The polymer sheet thus formed was removed from the mould and swollen with water or a borate buttered saline solution at pH 7.1 to form a hydrogel sheet. The starting formulation is suitable for the mould polymerisation of soft contact lenses.

EXAMPLE 6

Formation of 2(methacryloyloxyethyl)-2'(trimethylammonium)ethyl phosphate Inner Salt-co-2-hydroxyethyl-methacrylate-co-methylmethyacrylate-co-ethylenegycol-dimethacrylate Membrane The method of Example 5 was repeated just using 2(methacryloyloxyethyl)-2'(trimethylammonium)ethyl phosphate inner salt (compound C) (3.79 g), in 2-hydroxyethyl-methacrylate (8.39 g) together with methylmethacrylate (5.04 g), ethyleneglycoldimethacrylate (0.254 g) as crosslinking agent and azobisisobutyronitrile (0.15 g) as a polymerisation initiator.

The resultant hydrogel sheet is similar to that obtained in Example 5. The starting formulation is suitable for the mould polymerisation of soft contact lenses.

EXAMPLE 7

Formation of 2-(trimethylammonium)ethyl methacrylate trifluoromethane sulphate-co-2-hydroxyethylmethacrylate-co-methylene bis-acrylamide polymer Sheet 2-(trimethylammonium)ethyl methacrylate trifluoromethanesulphonate, compound A, (0.25 g) was dissolved in hydroxyethyl methacrylate (5 g) together with methylene bis-acrylamide (25 mg) as cross-linking agent and benzoyl peroxide (25 mg) as polymerisation initiator. The resulting monomer solution was then deoxygenated by bubbling nitrogen through for 5 minutes.

The monomer solution thus prepared was injected into a mould formed by two silylated glass plates separated by a teflon spacer. Polymerisation was carried out in situ by heating the mould to 70° C. and maintaining it at that temperature for 2 hours.

The polymer sheet formed was removed from the mould and swollen with water or a saline solution to form a hydrogel sheet, which is a material suitable for forming into soft contact lenses.

EXAMPLE 8

Preparation of Further Copolymers

The method of Example 6 was repeated using, respectively, each of compounds B and C and compound types D to G prepared as described in the Reference Examples in place of compound A. The hydrogel sheet formed in each case was suitable for forming into soft contact lenses.

Mechanical Testing of Copolymers

The copolymer sheets and lenses produced may be swelled in appropriate aqueous solutions and then dehydrated by heating. The water content may be determined by weight.

Tear strength measurement may be performed by Instrom analysis using appropriate ASTM procedures. Oxygen permeability may be determined with appropriate electrodes in accordance with appropriate ASTM standards. The absorption of tear proteins by the copolymers may be measured by standard spectrophometic techniques.

EXAMPLE 9

Lathe Cutting to Produce Contact Lenses

Buttons (as prepared in Example 1) were mounted using a low melting point wax and cut with a lathe speed of 2800 rpm to produce contact lenses. Cutting times were 1–2 seconds for 0.01 mm thickness reduction from the edge to the centre. Nitrogen may be used to cool the diamond button interface. The contact lenses produced were cleaned with petroleum ether (60–80) and polished with an oil based polish (SP2).

EXAMPLE 10

Protein Adsorption and Equilibrium Water Content Study

Two hydrogel membranes of comparable water content were prepared: membrane A (comparative) comprised of methacrylic acid (16.5 mole %), 2-hydroxyethylmethacrylate, (83.3 mole %) and ethyleneglycol dimethacrylate (0.2 mole %); membrane B according to the invention comprised of 2(methacryloyloxyethyl)-2'(trimethylammonium)ethyl phosphate inner salt (40% mole), methylmethacrylate (59 mole %) and ethylene glycol dimethacrylate (1%). Both membranes were cut into 0.9 mm discs and soaked in a buffered protein solution for 24 hours at 35° C. Control lenses were soaked in buffer solution for the same length of time. The buffer solution was the same as that of the buffered protein solution except that the bovine albumin and chicken lysozyme were not added.

The composition of the buffered protein solution was as follows:

| | |
|---|---|
| Sodium Chloride | 0.85% |
| Boric Acid | 0.46% |
| Sodium Borate (10 $H_2O$) | 0.04% |
| Bovine Albumin | 0.29% |
| Chicken Egg Lysozyme | 0.12% |
| Water | 98.4% |

The conditions chosen mimic the occular environment and are equivalent to those experienced by a contact lens during 7 days wear. The equilibrium water content was measured thermogravitmetrically and the dry weights of the membranes compared after soaking in the buffer solution and the buffered protein solution.

The equilibrium water content data and changes in dry weight equivalent to the adsorption of protein from the solution are shown below:

| Membrane | Equilibrium Water Content % | Increase in Dry Weight (g. Protein/g Polymer) |
|---|---|---|
| A at 35° C. | 79.4 ± 0.6 | — |
| A at 35° C. in protein solution | 75.9 ± 0.9 | 0.13 ± 0.04 |
| B At 35° C. | 70.5 ± 0.4 | — |
| B At 35° C. in protein solution | 71.1 ± 0.5 | 0.01 ± 0.05 |

The membrane containing 2(methacryloyloxyethyl)-2'(trimethylammonium)ethyl phosphate inner salt was found to absorb significantly less protein than a membrane material of comparable water content. The equilibrium water content also remained unchanged.

Reference Example 1

Synthesis of 2(trimethylammonium) ethylmethacrylate trifluoromethanesulphonate (Compound A)

2(Dimethylamino)ethylmethacrylate was vacuum distilled and then dissolved in 0.1M dichloromethane. Methyltrifluoromethyl sulphonate (one molar equivalent) was added slowly to the resulting solution, the temperature of the solution being maintained throughout at 40° C. or less. The product precipitated out slowly and was recovered by filtration and washed in cold dichloromethane. The synthesis is depicted in Reaction Scheme B.

Reference Example 2

Synthesis of dimethyl(2-methacryloxyethyl)-(1(2-sulphopropyl)) ammonium betaine Inner Salt (Compound B)

2(Dimethylamino)ethylmethacrylate was vacuum distilled and then dissolved in 0.1M dichloromethane. To this solution was added an equimolar amount of propane sultone. The betaine slowly precipitated out of solution and was recovered by filtration and washed with cold dichloromethane. The reaction is shown in Reaction Scheme B.

Reference Example 3

Preparation of 2(methacryloyloxyethyl)-2'(trimethylammonium ethyl phosphate Inner Salt (Compound C)

The preparation is illustrated by the reaction scheme C which follows.

a) 2-Chloro-1,3-dioxaphospholane (1)

In a flask fitted with a pressure equalising dropping funnel, reflux condenser (fitted with a $CaCl_2$ guard tube) and magnetic stirrer, was placed a solution of phosphorus trichloride (220 ml; 346.3 g; 2.52 mol) in dichloromethane (500 ml). Ethylene glycol (139 ml; 154.7 g, 2.49 mol) was then added dropwise via the dropping funnel at such a rate that the evolution of HCl did not become too excessive. On the addition of the ethylene glycol, the condenser was arranged for distillation, and the dichloromethane removed at atmospheric pressure. When the distillate temperature reached 60° C. the flask was arranged for vacuum distillation using a water pump, Distillation then gave 2-chloro-1,3-dioxaphospholane (158 ml; 224.5 g; 71.3%) as a colourless mobile liquid (which fumes in moist air) b.pt. 36–40° C./21 mm Hg. [cf 45.5–47° C./20 mm Hg, Lucas et al, J. Am. Chem. Soc., 72, 5491, (1950)].

IR (cm$^{-1}$, thin film) 2980, 2905, 1470, 1210, 1005, 930, 813, 770.

b) 2-Chloro-2-oxo-1,3,2-dioxaphospholane (2)

In a flask fitted with a magnetic stirrer, reflux condenser (fitted with a $CaCl_2$ guard tube) and sintered glass gas inlet tube, was placed a solution of 2-chloro-1,3-2-dioxaphospholane (100.8 g; 0.797 mol) in dry benzene (200 ml). The solution was stirred and a steady stream of oxygen was bubbled through the solution. The reaction was mildly exothermic, and temperature control was achieved by allowing the solvent to reflux. The oxygen was passed through the reaction mixture for 6 hours. The solvent was removed by rotary evaporation, and the colourless mobile residue distilled to give 2-chloro-2-oxo-1,3,2-dioxaphospholane (2) (87.41 g; 77%) as a colourless mobile liquid—b.pt 95–97° C./0.2 mbar [c.f. 102.5–105° C./1 mbar (Edmundson, Chem. Ind. (London)), 1828 (1962); 79° C./0.4 mbar (Umeda et al., Makromaol. Chem. Rapid Communo., 3, 457, (1982)].

IR(cm$^{-1}$, thin film) 2990, 2910, 1475, 1370, 1310, 1220, 1030, 930, 865, 830.

2(2-Oxo-1,3,2-dioxphospholan-2-yloxoy)ethyl methacrylate (3)

In a flask fitted with a magnetic stirrer, low temperature thermometer, and pressure equalising funnel fitted with a silica gel guard tube, was placed a solution of 2-hydroxyethylmethacrylate (20.00 g, 0.154 mol) and triethylamine (15.60 g; 0.154 mol) in dry diethyl ether (300 ml). The solution was stirred and cooled to between −20° C. and −30° C. A solution of freshly distilled 2-chloro-2-oxo-1,3,2-dioxaphospholane(2) (21.9 g; 0.154 mol) in dry diethyl ether (20 ml) was then added dropwise over 30 minutes, the temperature being held at −20° C. during the addition. Stirring was continued at this temperature for a further 1 hour and then for a further hour as the reaction mixture was allowed to warm to room temperature. The precipitated triethylamine hydrochloride was removed by filtration, and was washed well with dry ether. The ether was removed from the combined filtrate and washings by rotary evaporation. The cloudy oil residue was then shaken for 5 minutes with dry diethyl ether (50 ml) to precipitate a further crop of triethylamine hydrochloride, which was again removed by filtration. Removal of the ether on the rotary evaporator gave (3) (34.18 g; 94.3%) as a colourless viscous oil.

IR (cm$^{-1}$, thin film) 1720, 1640, 1450, 1360, 1310, 1290, 1170, 1030, 930, 850.

NMR (CDCl$_3$; 60 MHz, δ ppm) 1.95 (s,3H), 4.25–4.70 (m,8H), 5.70 (m,1H), 6.25 (m,1H).

Rf (SiO$_2$, eluting with 10% MeOH:90% CH$_2$Cl$_2$ −0.9; spot visualised with molybdenum blue spray reagent (eg Sigma), and with iodine vapour).

d) 2(Methyacryloyloxyethyl)-2(trimethylammonium)ethyl phosphate Inner Salt (4)

The phospholane (3) (67.20 g; 0.285 mol was dissolved in 100 ml of dry acetonitrile, and placed in a heavy walled tissue culture bottle. The phospholane solution was then treated with a solution of anhydrous trimethylamine (25.74 g; 0.436 mol) in dry acetonitrile (100 ml). The vessel was then sealed, and placed in a water bath held at 50° C. for 30 hours. The vessel was opened, and the solution brought to the boil. The solution was filtered whilst hot, and then set aside for crystallisation.

The product was collected by filtration, and most of the solvent removed by suction. The wet product was then washed thoroughly with anhydrous ether, then dried in vacuo, to give (4) as a white amorphous, hygroscopic solid (51.16 g; 61%). Evaporation of the mother liquor gave a very viscous oil (20.00 g; 23%), from which further product (4) crystallised on standing at −2° C. TLC (silica gel plates, eluting with MeOH/CH$_2$Cl$_2$ (1:1 v/v)) showed one spot Rf 0.1, which was revealed with Dragendorffs reagent, Molybdenum blue spray reagent, and iodine vapour.

IR(cm$^{-1}$ 1720, 1640, 1320, 1300, 1230, 1170, 970, 750.

NMR (D$_2$O; 60 MHz; δ ppm) 2.0 (s,3H), 3.27 (s,9H) 3.60–4.50 (m, 8H), 5.80, (m,1H) and 6.25 (m,1H).

CHN Found: C, 42.98%; H, 7.88%; N, 4.42%; P, 10.51%.
CHN Theory: C, 44.75%; H, 7.46%; N, 4.75%; P, 10.51%.

(d1) 2-(Methacryloyloxyethyl)-2'-(trimethylammonium) ethyl phosphate Inner Salt [Alternative Preparation]

Into a glass pressure bottle (300 cm$^3$), were placed 2-(2-oxo-1,3,2-dioxaphospholan-2-yloxy)ethyl methacrylate (10.0 g, 42 mmol) prepared in step (c) and dry acetonitrile (60 cm$^3$). The pressure bottle was cooled in cold water and then trimethylamine (2.5 g, 42 mmol) was rapidly added to the cold solution. The pressure bottle was closed and then shaken in a thermostat maintained at 55° C. for 2 hours. It was then allowed to come to room temperature and to stand overnight, and was shaken again at 55° C. for 13 hours. After the reaction it was cooled down in water to 10° C. It was rapidly filtered with filter paper. The filtrate was evaporated under reduced pressure with a stream of nitrogen for 2 hours to afford the product (12.3 g, 98%) as a colourless viscous liquid which crytallised on standing in a freezer. The product could be purified by preparative liquid chromatography.

Reference Example 4

1-alkanoyl-2-methacroyl phosphatidyl choline and 1-metharyloyl-2-alkanoyl phosphatidyl choline (Compound Types D and E)

Glycerophosphorylcholine (0.01 mole), obtained by base hydrolysis of natural phosphatidylcholine, may be stirred with alkynoic acid anhydride (0.01 mole) and dimethylamino pyridine (0.01 mole) in dimethylsulphoxide (150 cm$^3$).

At the conclusion of this reaction further dimethylamino pyridine (1 mole) together with methacrylic acid anhydride (1 mole) may be added. The resulting mixture may be stirred for 24 hours. The phosphatidylcholine formed may be purified by column chromatography on silica using a gradient elution procedure with chloroform:methanol:water.

The synthesis is depicted in reaction scheme D in which R=CH$_3$.

Reference Example 5

Synthesis of 1-alkanoyl-2-acroyl phosphatidylcholine and 1-acroyl-2-alkanoyl phosphatidylcholine (Compounds Type F and G)

The procedure of Reference Example 4 may be repeated, but with acrylic acid anhydride (1 mole) being used in place of methacrylic acid anhydride. The synthesis is depicted in Reaction Scheme D in which R=H.

Reference Example 6

Preparation of 1[4(4'-vinylbenzyloxy)butane]-2"-(trimethylammonium)ethyl phospate Inner Salt The synthesis is depicted in Reaction Scheme E.
4-Hydroxy-1(4'-vinylbenzyloxy)butane (5)

1,4-Butanediol (50.00 g) was dissolved in dry toluene (60 ml), para-choloromethylstyrene (15.62 g; 0.1 mol) was then added with stirring. A catalytic quantity of 18-crown-6 (0.3 g) was then added. The flask was stoppered, stirred at room temperature for 18 hours and for a further 4 hours at 45–60°. The resulting solution was then poured in to water (500 ml) and extracted with dichloromethane (3×75 ml). The combined extracts were dried (MgSO$_4$) and evaporated (20°/21 mm) to give a yellow oil, which was distilled to give a yellow oil (14.33 g; 69.6%).b.pt. 152–157°/1 mbar.

NMR (60 MHz: CDCl$_3$) 1.55 (m, 4H); 3.50 (m, 5H, 1H exch); 4.45, (s, 2H) 5.50 (dd, 2H), 6.75 (dd, 1H), 7.40 (m, 4H).

IR (thin film), 3402, 2938, 2888, 1631, 1602, 1582, 1511, 1480, 1445, 1382, 1320, 1116, 1063, 920, 907, 827, 801, 716 and 667 cm$^{-1}$.

4(2-Oxo-1,3,2-dioxaphospholane-2-yloxy)-1(4'-vinylbenyloxy)butane (6)

4-Hydroxy-1(4'-vinylbenzyloxy)butane (5) (10.03 g; 48.69 mmol) and dried triethylamine (4.92 g, 48.69 mmol)

were dissolved in dry diethyl ether (150 ml) and the resulting solution placed in a rigorously dried flask. The solution was cooled to −30° and 2-chloro-2-oxo-1,3,2-dioxaphospholane (6.94 g; 48.69 mmol) added dropwise over 30 minutes, the temperature being held at −30°. The reaction mixture was then stirred for a further 2 hours, during which time the temperature was allowed to rise to 100. The mixture was filtered and the precipitate washed with dry ether. The filtrate was evaporated (20°/21 mm) to give a cloudy oil. The residue was shaken with 50 ml of dry ether and refiltered. Evaporation of the filtrate gave the product as a viscous yellow oil (13.73 g; 90.4%).

TLC (eluting with 10% MeOH/90% dichloramethane) showed one major spot, which stained with acid molybdate reagent (Rf 0.61), IR (thin film) 3458, 2945, 2917, 2860, 1630, 1602, 1581, 1475, 1419, 1363, 1283, 1103, 1032, 820, 842, 807, 800, 715, 610 and 421 cm$^{-1}$.

1[4(4'-Vinylbenzyloxy)butane]-2"(trimethylammonium)ethyl phosphate Inner Salt (7)

Trimethylamine (2.00 g, 33.9 mmol) was distilled into a reaction vessel, and frozen with liquid nitrogen. A solution of the 4(2-oxo-1,3,2-dioxaphospholane-2-yloxy)-1-(4'-vinylbenyloxy)butane (6) (10.00 g, 32.1 mmol) in anhydrous acetonitrile (40 ml) was then added to the reaction vessel, which was then sealed and placed in a thermostatted water bath (50° for 50 hours). The reaction vessel was then cooled to room temperature, opened, and the reaction mixture evaporated to about half its original volume (21 mm pressure). The concentrated solution was then stirred at room temperature, whilst anhydrous ether (200 ml) was added dropwise to precipitate the product as a viscous oil. The mixture was then left for several hours at −10°. The product was collected by decanting off the supernatent solid. TLC (eluting with methanol/dichloromethane 1:1) showed one major spot at Rf 0.0–0.1 which stained with both Dragendorffs reagent and acid molybdate.

Reaction Scheme A

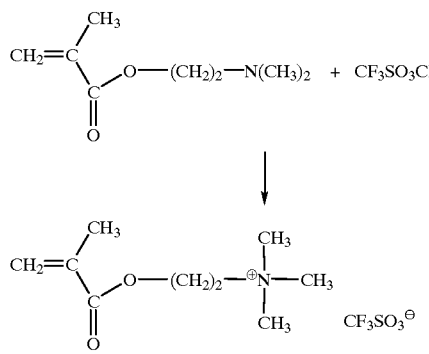

Reaction Scheme B

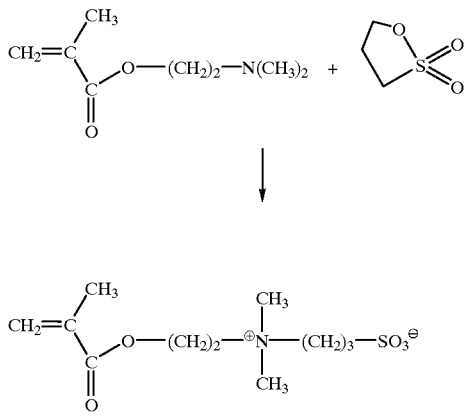

Reaction Scheme C

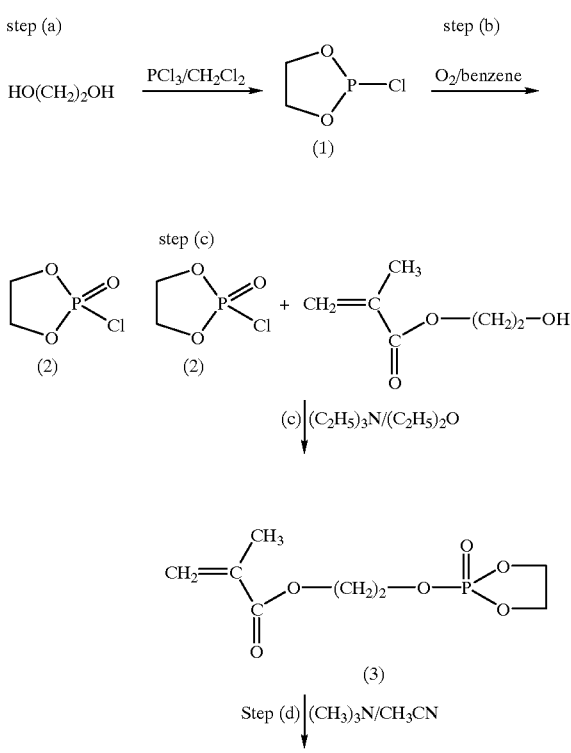

Steps (a) to (d) correspond with the steps in Reference Example 4

Reaction Scheme D
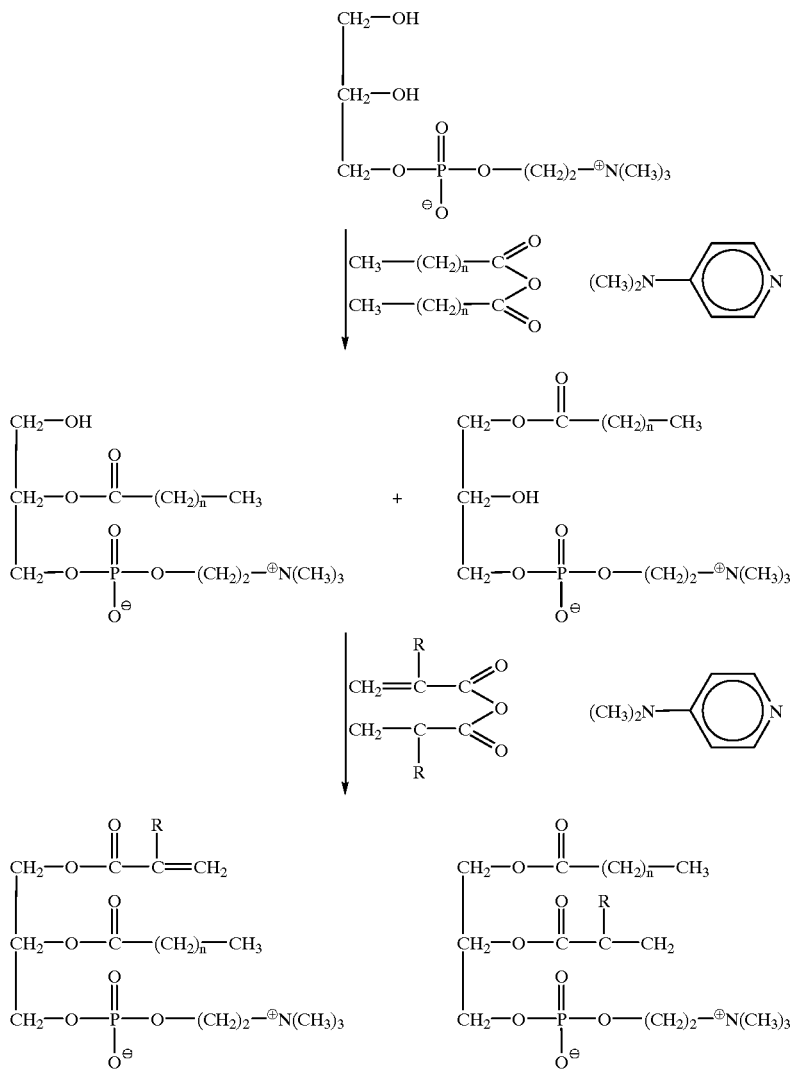
Reaction Scheme E
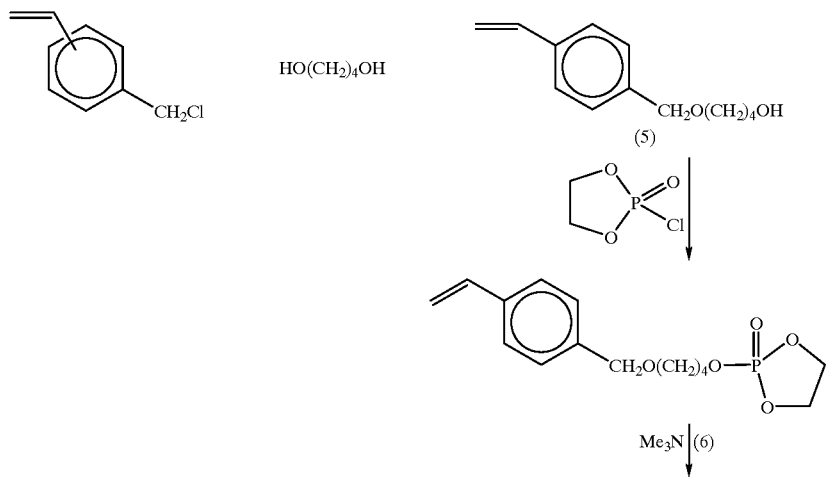

-continued

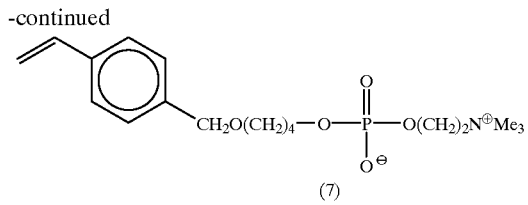

(7)

What is claimed is:

1. A cross-linked polymer obtained by polymerizing a mixture consisting essentially of:
   i) a zwitterionic monomer of the formula (V):

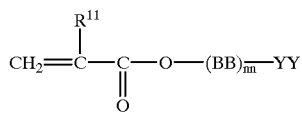

(V)

wherein BB is a straight or branched $C_1$–$C_6$ alkylene chain optionally interrupted by one or more oxygen atoms:
nn is from 1 to 12;
$R^{11}$ is H or a $C_1$–$C_4$ alkyl group; and
YY is a zwitterionic group which is selected from the group consisting of:

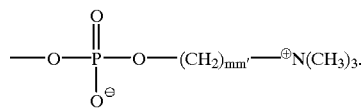

(VIC)

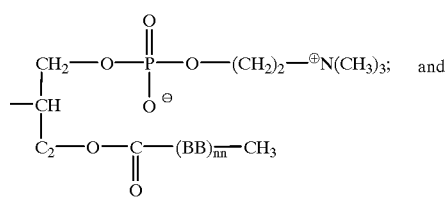

(VID)

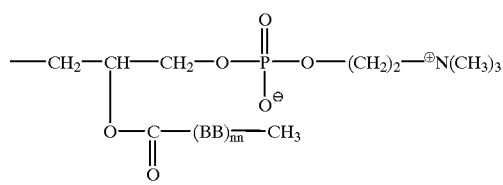

(VIE)

wherein mm is 1 to 4, nn is 1 to 12 and BB is a straight or branched $C_1$–$C_6$ alkylene chain optionally interrupted by one or more oxygen atoms;
   ii) a non-ionic diluent monomer; and
   iii) a cross-linking monomer which forms cross-links during the polymerization reaction.

2. A cross-linked polymer according to claim 1, in which the diluent monomer is selected from the group consisting of alkyl (alk)acrylates, dialkylamino alkyl (alk)acrylates, alkyl (alk)acrylamides, hydroxyalkyl (alk)acrylates, N-vinyl lactams, styrene, substituted styrene, and mixtures thereof.

3. A cross-linked polymer according to claim 2, in which the diluent monomer is selected from the group consisting of vinylpyrrolidone, 2-hydroxyethylmethacrylate, methylmethacrylate and mixtures thereof.

4. A cross-linked polymer according to claim 3 wherein the diluent monomer is 2-hydroxyethylmethacrylate.

5. A cross-linked polymer according to claim 3, wherein the diluent monomer is methylmethacrylate.

6. A cross-linked polymer according to claim 1, in which the cross-linking monomer is a bifunctional or trifunctional cross-linking agent.

7. A cross-linked polymer according to claim 6, in which the cross-linking monomer is selected from the group consisting of ethyleneglycoldimethacrylate, trimethylolpropane trimethacrylate and N,N'-methylenebisacrylamide.

8. A cross-linked copolymer according to claim 1, in which YY is a group of formula (VIC).

9. A cross-linked polymer according to claim 1, in which YY is a group of formula (VID).

10. A cross-linked polymer according to claim 1, in which the group YY is a group of formula (VIE).

11. A cross-linked polymer according to claim 1, wherein the group $R^{11}$ is hydrogen or methyl.

12. A cross-linked polymer according to claim 1, in which the zwitterionic monomer of the formula V is 2(methacryloyloxy)ethyl-2'-(trimethylammonium)ethyl phosphate inner salt.

13. A cross-linked polymer according to claim 12, in which the diluent monomer is 2-hydroxyethylmethacrylate.

14. A hydrogel comprising a cross-linked polymer according to claim 1, and water in an amount of from 30 to 80% by weight of the hydrogel.

15. A xerogel comprising a cross-linked polymer according to claim 1, which is free of water.

16. A cross-linked polymer obtained by polymerizing a mixture consisting essentially of;
   i) a zwitterionic monomer of formula (I):

Y—B—X  (I)

wherein B is a straight or branched alkylene, oxaalkylene or oligo-oxaalkylene chain or if X contains a carbon-carbon chain between B and the zwitterionic group or if K is joined to B via a carbon atom, a valence bond,
   Y is an ethylenically unsaturated polymerizable group selected from:

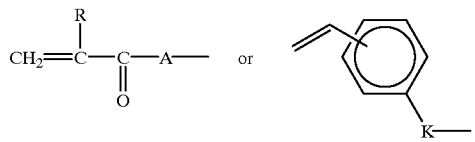

wherein:
   R is hydrogen or a $C_1$–$C_4$ alkyl group;
   A is —O— or —$NR^1$— where $R^1$ is hydrogen or a $C_1$–$C_4$ alkyl group or $R^1$ is —B—X where B and X are as defined above; and
   K is a group —$(CH_2)_pOC(O)$—, —$(CH_2)_pC(O)O$—, —$(CH_2)_pOC(O)O$—, —$(CH_2)_pNR^2$—, —(CH$_2$)$_p$NR$^2$C(O)—, —(CH$_2$)$_p$C(O)NR$^2$—, —(CH$_2$)$_p$NR$^2$C(O)O—, —(CH$_2$)$_p$NR$^2$C(O)O—, —(CH$_2$)$_p$OC(O)NR$^2$—, —(CH$_2$)$_p$NR$^2$C(O)NR$^2$— (in which the groups R$^2$ are the same or different), —(CH$_2$)$_p$O—, —(CH$_2$)$_p$SO$_3$—, or, optionally in a combination with B, a valence bond, and p is from 1 to 12 and R$^2$ is hydrogen or a C$_1$–C$_4$ alkyl group and X is selected from the group consisting of groups of formula (IVC):

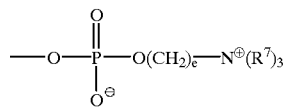
(IVC)

wherein the groups R$^7$ are the same or different and each is hydrogen or C$_{1-4}$ alkyl, and e is 1, 3 or 4;

groups of formula (IVD):

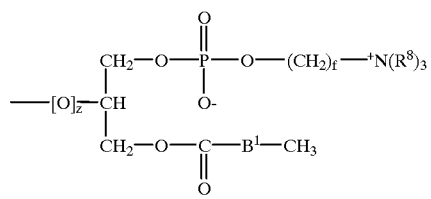
(IVD)

wherein the groups R$^8$ are the same or different and each is hydrogen or C$_{1-4}$ alkyl, B$^1$ is a valence bond or straight or branched alkylene, oxaalkylene or oligo-oxaalkylene group, f is from 1 to 4 and if B is other than a valence bond, z is 1 and if B is a valence bond z is 0 if X is directly bonded to an oxygen or nitrogen atom and otherwise z is 1;

groups of formula (IVE):

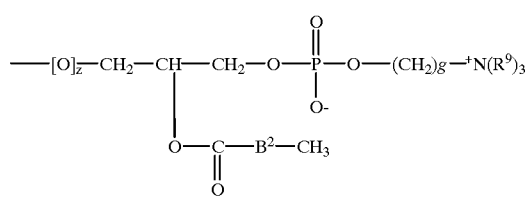
(IVE)

wherein the groups R$^9$ are the same or different and each is hydrogen or C$_{1-4}$ alkyl, B$^2$ is a valence bond or a straight or branched alkylene, oxaalkylene or oligo-oxaalkylene group, g is from 1 to 4 and if B is other than a valence bond, z is 1 and if B is a valence bond z is 0 if X is directly bonded to an oxygen or nitrogen atom and otherwise z is 1; and groups of formula (IVF):

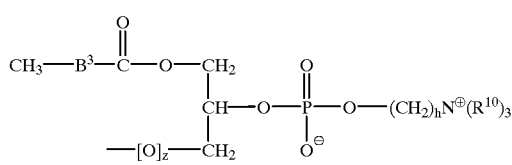
(IVF)

wherein the groups R$^{10}$ are the same or different and each is hydrogen or C$_{1-4}$ alkyl, B$^3$ is a valence bond or a straight or branched alkylene, oxaalkylene or oligo-oxaalkylene group, h is from 1 to 4 if B is other than a valence bond, z is 1 and if B is a valence bond z is 0 if X is directly bonded to an oxygen or nitrogen atom and otherwise z is 1;

ii) a non-ionic diluent monomer; and iii) a cross-linking monomer which forms cross-links during the polymerization reaction.

17. A cross-linked polymer according to claim 16, in which the diluent monomer is selected from the group consisting of alkyl (alk)acrylates, dialkylamino alkyl (alk)acrylates, alkyl (alk)acrylamides hydroxyalkyl (alk)acrylates, N-vinyl lactams, styrene, substituted styrene; and mixtures thereof.

18. A cross-linked polymer according to claim 17, in which the diluent monomer is selected from the group consisting of vinylpyrrolidone, 2-hydroxyethylmethacrylate, methylmethacrylate and mixtures thereof.

19. A cross-linked polymer according to claim 16, in which B is an alkylene group of formula —(CR$^3{}_2$)$_a$—, wherein the groups —(CR$^3{}_2$)— are the same or different, and in each group —(CR$^3{}_2$)— the groups R$^3$ are the same or different and each group R$^3$ is hydrogen or C$_1$–C$_4$ alkyl, and a is from 1 to 12;

an alkoxyalkyl group having 1 to 6 carbon atoms in each alkyl moiety;

an oligo-oxaalkylene group of formula —[(CR$^4{}_2$)$_b$O]$_c$(CR$^4{}_2$)$_b$— where the groups —(CR$^4{}_2$)— are the same or different and in each group —(CR$^4{}_2$)— the groups R$^4$ are the same or different and each group R$^4$ is hydrogen or C$_1$–C$_4$ alkyl, and b is 2 or 3 and c is from 2 to 11, or if X contains a carbon-carbon chain between B and the center of positive charge, or if K is joined to B via a carbon atom, a valence bond.

20. A cross-linked polymer according to claim 16, in which X is a group of formula (IVD), (IVE) or (IVF) and B$^1$, B$^2$ or B$^{31}$, respectively, contains up to 24 carbon atoms.

21. A cross-linked polymer according to claim 16, in which the group X is a group of formula (IVC).

22. A cross-linked polymer according to claim 21, wherein the groups R$^7$ are all methyl.

23. A cross-linked polymer according to claim 16, in which cross-linking monomer is a bifunctional or trifunctional cross-linking agent.

24. A cross-linked polymer according to claim 23, in which the cross-linking agent is selected from the group consisting of ethyleneglycoldimethacrylate, trimethylolpropanetrimethacrylate and N,N'-methylenebisacrylamide.

25. A hydrogel comprising a cross-linked polymer according to claim 16, and water in an amount of from 30 to 80% by weight of the hydrogel.

26. A xerogel comprising a cross-linked polymer according to claim 16 which is free of water.

27. A process for producing a cross-linked copolymer by copolymerizing a monomer solution consisting essentially of a non-ionic diluent monomer or monomers, a zwitterionic monomer or monomers and a cross-linking monomer, wherein said zwitterionic monomer or monomers has the formula (V):

(V)

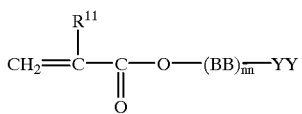

wherein BB is a straight or branched $C_1$–$C_6$ alkylene chain optionally interrupted by one or more oxygen atoms:
nn is from 1 to 12;
$R^{11}$ is H or a $C_1$–$C_4$ alkyl group; and
YY is a zwitterionic group which is selected from the group consisting of:

(VIC)

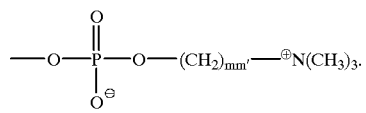

(VID)

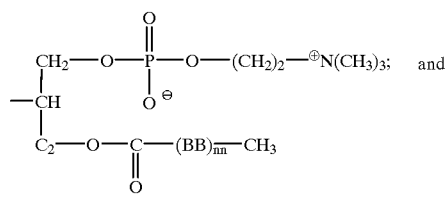  and (VIE)

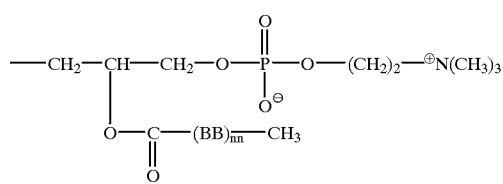

wherein mm is 1 to 4, nn is 1 to 12 and BB is a straight or branched $C_1$–$C_6$ alkylene chain optionally interrupted by one or more oxygen atoms.

28. A process for producing a cross-linked copolymer by copolymerizing a monomer solution consisting essentially of a non-ionic diluent monomer or monomers, a zwitterionic monomer or monomers and a cross-linking monomer, wherein said zwitterionic monomer or monomers has the formula (I)

Y—B—X (I)

wherein B is a straight or branched alkylene, oxaalkylene or oligo-oxaalkylene chain or if X contains a carbon-carbon chain between B and the zwitterionic group or if K is joined to B via a carbon atom, a valence bond;
Y is an ethylenically unsaturated polymerizable group selected from:

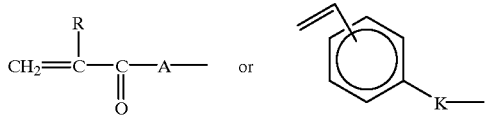

wherein:
R is hydrogen or a $C_1$–$C_4$ alkyl group;
A is —O— or —$NR^1$— wherein $R^1$ is hydrogen or a $C_1$–$C_4$ alkyl group or $R^1$ is —B—X where B and X are as defined above; and K is a group —$(CH_2)_pOC(O)$—, —$(CH_2)_pC(O)O$—, —$(CH_2)_pOC(O)O$—, —$(CH_2)_pNR^2$—, —$(CH_2)_pNR^2C(O)$—, —$(CH_{2p}C(O)NR^2$—, —$(CH_2)_pNR^2C(O)O$—, —$(CH_2)_pNR^2C(O)O$—, —$(CH_2)_pOC(O)NR^2$—, —$(CH_2)_pNR^2C(O)NR^2$— (in which the groups $R^2$ are the same or different), —$(CH_2)_pO$—, —$(CH_2)_pSO_3$—, or, optionally in a combination with B, a valence bond, and p is from 1 to 12 and $R^2$ is hydrogen or a $C_1$–$C_4$ alkyl group and X is selected from the group consisting of groups of formula (IVC):

(IVC)

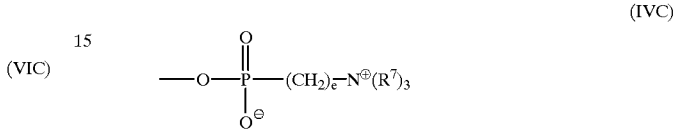

wherein the groups $R^7$ are the same or different and each is hydrogen or $C_{1-4}$ alkyl, and e is 1, 3 or 4:

groups of formula (IVD):

(IVD)

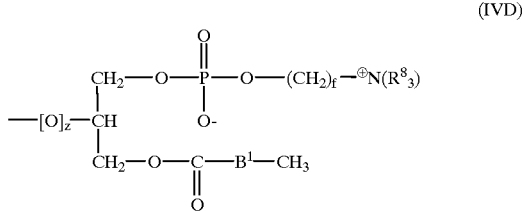

wherein the groups $R^8$ are the same or different and each is hydrogen or $C_{1-4}$ alkyl, $B^1$ is a valence bond or straight or branched alkylene, oxaalkylene or oligo-oxaalkylene group, f is from 1 to 4 and if B is other than a valence bond, z is 1 and if B is a valence bond z is 0 if X is directly bonded to an oxygen or nitrogen atom and otherwise z is 1;

groups of formula (IVE):

(IVE)

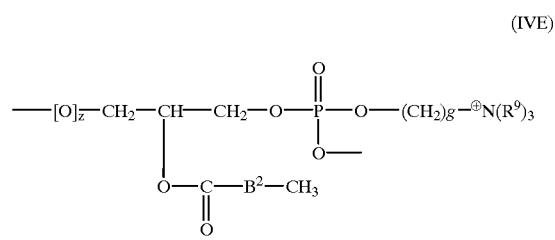

wherein the groups $R^9$ are the same or different and each is hydrogen or $C_{1-4}$ alkyl, $B^2$ is a valence bond or a straight or branched alkylene, oxaalkylene or oligo-oxaalkylene group, g is from 1 to 4 and if B is other than valence bond, z is 1 and if B is a valence bond z is 0 if X is directly bonded to an oxygen or nitrogen atom and otherwise z is 1; and groups of formula (IVF):

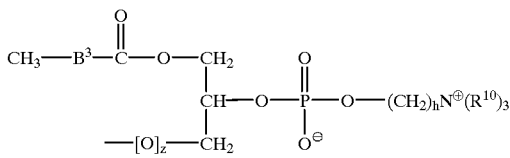

wherein the groups $R^{10}$ are the same or different and each is hydrogen or $C_{1-4}$ alkyl, $B^3$ is a valence bond or a straight or branched alkylene, oxaalkylene or oligo-oxaalkylene group, h is from 1 to 4 if B is other than a valence bond, z is 1 and if B is a valence bond z is 0 if X is directly bonded to an oxygen or nitrogen atom and otherwise z is 1.

29. A process according to claim 27, in which the zwitterionic monomer or monomers and diluent monomer or monomers are immiscible and in which the reaction mixture for the polymerization includes a solvent in which all the monomers are dissolved.

30. A process according to claim 27, in which the diluent monomer or monomers comprises alkyl(alk)acrylate having 1–12 carbon atoms in the alkyl group.

31. A process according to claim 30, in which the diluent monomer is methylmethacrylate.

32. A process according to claim 31, in which the solvent is selected from ethanol, methanol and water.

33. A process according to claim 27 in which the reaction mixture is free of water such that the polymerization produces a xerogel and in which the xerogel is hydrated with water to produce a hydrogel containing from 30 to 80% water.

34. A process according to claim 32, in which the solvent is present in an amount in the range of 5–40 wt % based on the total reaction mixture.

35. A process according to claim 27, in which the comonomers are miscible.

36. A process according to claim 35, in which the polymerization mixture is substantially free of solvent and of non-polymerizable diluent.

37. A process according to claim 36 in which after polymerization the cross-linked polymer is hydrated to form a hydrogel containing from 30 to 80% by weight water.

38. A process according to claim 35, in which the diluent monomer comprises hydroxy alkyl(alk)acrylate in which the hydroxy alkyl group contains in the range of from 1–4 carbon atoms.

39. A process according to claim 38, in which the diluent monomer is 2-hydroxyethylmethacrylate.

40. A process according to claim 27, in which the cross-linking agent is a bifunctional or trifunctional monomer.

41. A process according to claim 40, in which the cross-linking agent is selected from the group consisting of ethyleneglycoldimethacrylate, trimethylolpropanetrimethacrylate and N,N'-methylene bisacrylamide.

42. A process according to claim 27, in which the cross-linking agent is present in an amount of 0.10 to 10% by weight based upon total monomer weight.

43. A process according to claim 27, in which YY is a group of formula (VIC).

44. A process according to claim 27, in which YY is a group of formula (VID).

45. A process according to claim 27, in which the group YY is a group of formula (VIE).

46. A process according to claim 27, wherein the group $R^{11}$ is hydrogen or methyl.

47. A process according to claim 27, in which the zwitterionic monomer of the formula V is 2-(methacryloyloxyethyl)-2'-(trimethylammonium)ethyl phosphate inner salt.

48. A process according to claim 27, in which the diluent monomer is 2-hydroxyethyl methacrylate.

49. A process according to claim 28, in which the zwitterionic monomer or monomers and diluent monomer or monomers are immiscible and in which the reaction mixture for the polymerization includes a solvent in which all the monomers are dissolved.

50. A process according to claim 49, in which the diluent monomer or monomers comprises alkyl(alk)acrylate having 1–12 carbon atoms in the alkyl group.

51. A process according to claim 50, in which the diluent monomer is methylmethacrylate.

52. A process according to claim 49, in which the solvent is selected from ethanol, methanol and water.

53. A process according to claim 49, in which the reaction mixture is free of water such that the polymerization produces a xerogel and in which the xerogel is hydrated to from a hydrogel containing from 30 to 80% of water.

54. A process according to claim 28, in which the solvent is present in an amount in the range of 5–40 wt % based on the total reaction mixture.

55. A process according to claim 28, in which the comonomers are miscible.

56. A process according to claim 55, in which the polymerization mixture is substantially free of solvent and of non-polymerization diluent.

57. A process according to claim 55, in which after polymerization the cross-linked polymer is hydrated to form a hydrogel containing from 30 to 80% by weight water.

58. A process according to claim 55, in which the diluent monomer comprises hydroxy alkyl(alk)acrylate in which the hydroxy alkyl group contains in the range of from 1–4 carbon atoms.

59. A process according to claim 58, in which the diluent monomer is 2-hydroxyethylmethacrylate.

60. A process according to claim 28, in which the cross-linking agent is a bifunctional or trifunctional monomer.

61. A process according to claim 60, in which the cross-linking agent is selected from the group consisting of ethyleneglycoldimethacrylate, trimethylolpropanetrimethacrylate, and N,N'-methylene bisacrylamide.

62. A process according to claim 28, in which the cross-linking agent is present in an amount in the range 0.1 to 10% by weight based upon total monomer weight.

63. A process according to claim 28, in which X is a group of formula (IVC).

64. A process according to claim 28, in which X is a group of formula (IVD).

65. A process according to claim 28, in which the group X is a group of formula (IVE).

66. A process according to claim 28, wherein the group $R^{11}$ is hydrogen or methyl.

67. A contact lens material comprising a cross-linked polymer obtained by polymerizing a mixture consisting essentially of:

31 i) a zwitterionic monomer of the formula (V):

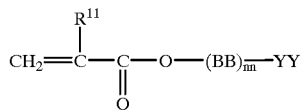
(V)

wherein BB is a straight or branched $C_1$–$C_6$ alkylene chain optionally interrupted by one or more oxygen atoms:

nn is from 1 to 12;

$R^{11}$ is H or a $C_1$–$C_4$ alkyl group; and

YY is a zwitterionic group VIB

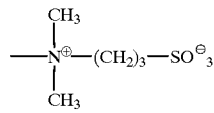
(VIB)

ii) a non-ionic diluent monomer; and iii) a cross-linking monomer which forms cross-links during the polymerization reaction selected from the group consisting of alkane diol di(alk)acrylates, alkane triol tri(alk)acrylates, alkylene di(alk)acrylamides, alkylene tri(alk)acrylamides, divinylbenzene, and trivinylbenzene.

68. A contact lens material comprising a cross-linked polymer obtained by polymerizing a mixture consisting essentially of:

i) a zwitterionic monomer of formula (I):

(I)

wherein B is a straight or branched alkylene, oxaalkylene or oligooxaalkylene chain or if X contains a carbon-carbon chain between B and the zwitterionic group or it Y contains a terminal carbon atom, a valence bond, Y is an ethylenically unsaturated polymerizable group selected from:

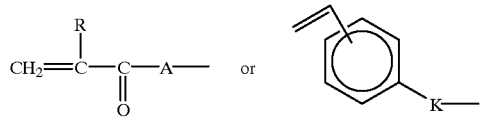

wherein:

R is hydrogen or a $C_1$–$C_4$ alkyl group;

A is —O— or —$NR^1$— where $R^1$ is hydrogen or a $C_1$–$C_4$ alkyl group or $R^1$ is —B—X where B and X are defined above; and K is a group —$(CH_2)_pOC(O)$—, —$(CH_2)_pC(O)O$—, —$(CH_2)_FOC(O)O$—, —$(CH_2)_pNR^2$—, —$(CH_2)_pNR^2C(O)$—, —$(CH_2)_pC(O)NR^2$—, —$(CH_2)_pNR^2C(O)O$—, —$(CH_2)_pNR^2C(O)O$—, —$(CH_2)_pOC(O)NR^2$—, —$(CH_2)_pNR^2C(O)NR^2$—, (in which the groups $R^2$ are the same or different), —$(CH_2)_pO$—, —$(CH_2)_pSO_3$—, or, optionally in a combination with B, a valence bond, and p is from 1 to 12 and $R^2$ is hydrogen or a $C_1$–$C_4$ alkyl group and X is IVB

32

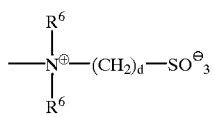
(IVB)

wherein the groups $R^6$ are the same or different and each is hydrogen or $C_{104}$ alkyl and d is from 2 to 4, II ii) a non-ionic diluent monomer; and iii) a cross-linking monomer which forms cross-links during the polymerization reaction selected from the group consisting of alkane diol di(alk)acrylates, alkane triol tri(alk)acrylates, alkylene di(alk)acrylamides, alkylene tri(alk)acrylamides, divinylbenzene, and trivinylbenzene.

69. A contact lens which is a hydrogel formed from a contact lens material according to claim 67 or 68 and water in an amount from 30 to 80% by weight.

70. A cross-linked polymer according to claim 1 obtained by polymerizing at least 0.2% by weight of said zwitterionic monomer at least 70% by weight of said diluent monomer, and at least 0.01% by weight of said cross-linking monomer, said weight proportions being based on the total weight of monomer.

71. A cross-linked polymer according to claim 16, obtained by polymerizing at least 0.2% by weight of said zwitterionic monomer at least 70% by weight of said diluent monomer, and at least 0.01% by weight of said cross-linking monomer, said weight proportions being based on the total weight of monomer.

72. A process according to claim 27, wherein said copolymerization comprises copolymerizing at least 70% by weight of said non-ionic diluent monomer or monomers, at least 0.2% by weight of said zwitterionic monomer or monomers and at least 0.01% by weight of said cross-linking agent, said weight proportions being based on the total weight of monomers.

73. A process according to claim 28, wherein said copolymerization comprises copolymerizing at least 70% by weight of said non-ionic diluent monomer or monomers, at least 0.2% by weight of said zwitterionic monomer or monomers and at least 0.01% by weight of said cross-linking agent, said weight proportions being based on the total weight of monomers.

74. A crosslinked polymer obtained by polymerizing a mixture consisting essentially of:

i) a zwitterionic monomer of formula (I):

(I)

wherein B is a straight or branched alkylene, oxaalkylene or oligo-oxaalkylene chain, Y is a group of formula

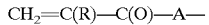

wherein:

R is hydrogen or a $C_1$–$C_4$ alkyl group;

A is —O— or —$NR^1$— where $R^1$ is hydrogen or a $C_{1-4}$-alkyl group or $R^1$ is —B—X where B is defined above and X is as defined below; and X is selected from the group consisting of groups of formula (IVC):

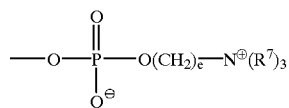

wherein the groups $R^7$ are the same or different and each is hydrogen or $C_{1-4}$ alkyl, and e is 1, 3 or 4;

groups of formula (IVD):

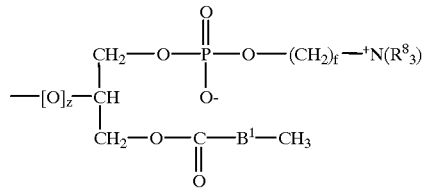

wherein the groups $R^8$ are the same or different and each is hydrogen or $C_{1-4}$ alkyl, $B^1$ is a valence bond or straight or branched alkylene, oxaalkylene or oligo-oxaalkylene group, f is from 1 to 4 and z is 1;

groups of formula (IVE):

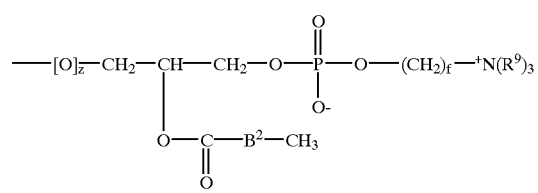

wherein the groups $R^9$ are the same or different and each is hydrogen or $C_{1-4}$ alkyl, $B^2$ is a valence bond or a straight or branched alkylene, oxaalkylene or oligo-oxaalkylene group, g is from 1 to 4 and z is 1; and groups of formula (IVF):

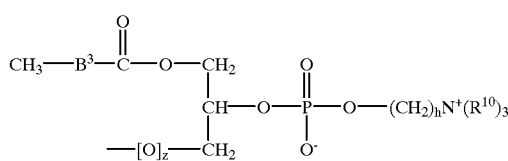

wherein the groups $R^{10}$ are the same or different and each is hydrogen or $C_{1-4}$ alkyl, $B^3$ is a valence bond or a straight or branched alkylene, oxaalkylene or oligo-oxaalkylene group, h is from 1 to 4 and z is 1;

ii) a non-ionic diluent monomer; and iii) a cross-linking monomer which forms cross-links during the polymerization reaction.

75. A process for producing a crosslinked copolymer by copolymerizing a solution containing mixture of monomers consisting essentially of a non-ionic diluent monomer or monomers, a zwitterionic monomer or monomers and a crosslinking monomer, wherein said zwitterionic monomer or monomers has the formula (I):

$$Y\text{—}B\text{—}X \quad (I)$$

wherein B is a straight or branched alkylene, oxaalkylene or oligo-oxaalkylene chain, Y is a group of formula $$CH_2{=}C(R)\text{—}C(O)\text{—}A\text{—}$$

wherein:

R is hydrogen or a $C_1$–$C_4$ alkyl group;

A is —O— or —$NR^1$— where $R^1$ is hydrogen or a $C_{1-4}$-alkyl group or $R^1$ is —B—X where B is defined above and X is as defined below; and X is selected from the group consisting of groups of formula (IVC):

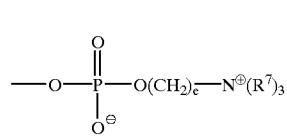

wherein the groups $R^7$ are the same or different and each is hydrogen or $C_{1-4}$ alkyl, and e is 1, 3 or 4;

groups of formula (IVD):

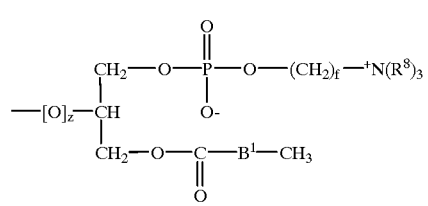

wherein the groups $R^8$ are the same or different and each is hydrogen or $C_{1-4}$ alkyl, $B^1$ is a valence bond or straight or branched alkylene, oxaalkylene or oligo-oxaalkylene group, f is from 1 to 4 and z is 1;

groups of formula (IVE):

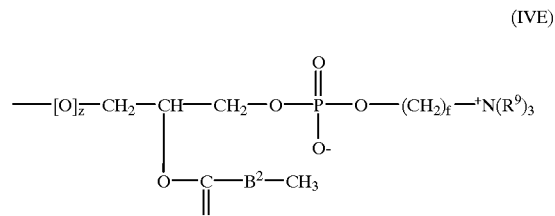

wherein the groups $R^9$ are the same or different and each is hydrogen or $C_{1-4}$ alkyl, $B^2$ is a valence bond or a straight or branched alkylene, oxaalkylene or oligo-oxaalkylene group, g is from 1 to 4 and z is 1; and groups of formula (IVF):

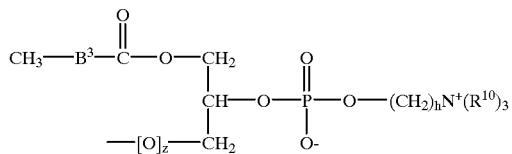

(IVF)

wherein the groups $R^{10}$ are the same or different and each is hydrogen or $C_{1-4}$ alkyl, $B^3$ is a valence bond or a straight or branched alkylene, oxaalkylene or oligo-oxaalkylene group, h is from 1 to 4 and z is 1;

ii) a non-ionic diluent monomer; and
iii) a cross-linking monomer which forms cross-links during the polymerization reaction.

76. A contact lens material according to claim 67 in which the nonionic diluent monomer is selected from the group consisting of alkyl(alk)acrylates containing 1 to 12 carbon atoms in the alkyl group; hydroxy alkyl(alk)acrylate containing from 1 to 4 carbon atoms in the hydroxy alkyl group, N-vinyl lactam containing from 5 to 7 atoms in the lactam ring, styrene and alkyl(alk)acrylamides containing 1 to 4 carbon atoms in the alkyl group.

77. A contact lens material according to claim 68 in which the nonionic diluent monomer is selected from the group consisting of alkyl(alk)acrylates containing 1 to 12 carbon atoms in the alkyl group; hydroxy alkyl(alk)acrylate containing from 1 to 4 carbon atoms in the hydroxy alkyl group, N-vinyl lactam containing from 5 to 7 atoms in the lactam ring, styrene and alkyl(alk)acrylamides containing 1 to 4 carbon atoms in the alkyl group.

* * * * *

UNITED STATES PATENT AND TRADEMARK OFFICE
CERTIFICATE OF CORRECTION

PATENT NO.    : 6,423,761 B1
DATED         : July 23, 2002
INVENTOR(S)   : Roderick Bowers It is certified that error appears in the above-identified patent and that said Letters Patent is hereby corrected as shown below:

Column 23,
Line 32, formula (VIC), delete

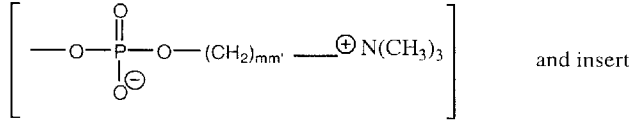    and insert

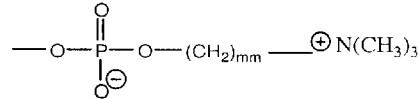

Column 26,
Line 43, delete "[$B^{31}$]" and insert -- $B^3$ --.

Column 27,
Line 18, formula (VIC), delete

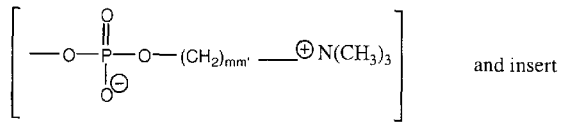    and insert

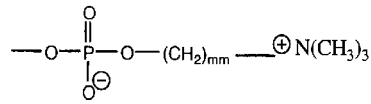

Signed and Sealed this

Twentieth Day of January, 2004

JON W. DUDAS
*Acting Director of the United States Patent and Trademark Office*